(12) United States Patent
Couture

(10) Patent No.: US 10,874,408 B2
(45) Date of Patent: Dec. 29, 2020

(54) PATIENT-SPECIFIC INSTRUMENTATION FOR PATELLAR RESURFACING SURGERY AND METHOD

(71) Applicant: ZIMMER, INC., Warsaw, IN (US)

(72) Inventor: Pierre Couture, Montreal (CA)

(73) Assignee: ZIMMER, INC, Warsaw, IN (US)

( * ) Notice: Subject to any disclaimer, the term of this patent is extended or adjusted under 35 U.S.C. 154(b) by 207 days.

(21) Appl. No.: 15/282,467

(22) Filed: Sep. 30, 2016

(65) Prior Publication Data
US 2017/0086859 A1 Mar. 30, 2017

Related U.S. Application Data

(60) Provisional application No. 62/235,111, filed on Sep. 30, 2015.

(51) Int. Cl.
*A61B 17/17* (2006.01)
*A61B 34/10* (2016.01)
(Continued)

(52) U.S. Cl.
CPC ........ *A61B 17/1767* (2013.01); *A61B 17/158* (2013.01); *A61B 34/10* (2016.02);
(Continued)

(58) Field of Classification Search
CPC ............ A61B 17/1767; A61B 17/1677; A61B 17/158
(Continued)

(56) References Cited

U.S. PATENT DOCUMENTS

| | | | |
|---|---|---|---|
| 4,841,975 A | 6/1989 | Woolson | |
| 5,098,383 A | 3/1992 | Hemmy et al. | |

(Continued)

FOREIGN PATENT DOCUMENTS

| | | |
|---|---|---|
| AU | 2004293091 A1 | 6/2005 |
| AU | 2004293104 A1 | 6/2005 |

(Continued)

OTHER PUBLICATIONS

Taylor et al, "Computer-Integrated Surgery, Technology and Clinical Applications", The MIT Press, Cambridge, MA, London, UK, pp. 451-463.

(Continued)

*Primary Examiner* — Amy R Sipp
(74) *Attorney, Agent, or Firm* — Norton Rose Fulbright Canada LLP

(57) ABSTRACT

A system for creating a patient-specific jig model for patellar resurfacing surgery comprises a patellar implant positioning module for obtaining a planned position of a patellar implant on a model of the patella, the model being anatomically patient-specific. A patella resurfacing calculator module calculates a position and/or orientation of a resurfacing plane and attachment bore in the patella as a function of the planned position of the patellar implant. A jig model generator module for generates and outputs a virtual jig model using the resurfacing plane and attachment bore of the patella and the model of the patella, the jig model comprising at least one patient-specific contact surface corresponding to a surface of the patella for complementary contact, at least one drill guide positioned relative to the at least one patient-specific contact surface to be configured to guide a tool defining the attachment bore for the patellar implant, and at least one cut guide positioned relative to the at least one patient-specific contact surface to be configured to guide a tool in resurfacing the patella to form the planned resurfacing plane.

12 Claims, 11 Drawing Sheets

(51) Int. Cl.
   *A61B 17/15* (2006.01)
   *A61B 17/00* (2006.01)
(52) U.S. Cl.
   CPC .............. *A61B 2017/00526* (2013.01); *A61B 2034/102* (2016.02); *A61B 2034/105* (2016.02); *A61B 2034/108* (2016.02)
(58) Field of Classification Search
   USPC .................................................. 606/88, 86 R
   See application file for complete search history.

(56) References Cited

U.S. PATENT DOCUMENTS

| | | |
|---|---|---|
| 5,490,854 A | 2/1996 | Fisher et al. |
| 5,768,134 A | 6/1998 | Swaelens et al. |
| 5,871,018 A | 2/1999 | Delp et al. |
| 5,916,219 A | 6/1999 | Matsuno et al. |
| 6,855,150 B1 * | 2/2005 | Linehan ............. A61B 17/1767 606/96 |
| 7,357,057 B2 | 4/2008 | Chiang |
| 7,468,075 B2 | 12/2008 | Lang et al. |
| 7,510,557 B1 | 3/2009 | Bonutti |
| 7,534,263 B2 | 5/2009 | Burdulis |
| 7,618,451 B2 | 11/2009 | Berez et al. |
| 7,634,119 B2 | 12/2009 | Tsougarakis et al. |
| 7,717,956 B2 | 5/2010 | Lang |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,806,897 B1 | 10/2010 | Bonutti |
| 7,967,868 B2 | 6/2011 | White et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,070,752 B2 | 12/2011 | Metzger et al. |
| 8,077,950 B2 | 12/2011 | Tsougarakis et al. |
| 8,083,745 B2 | 12/2011 | Lang et al. |
| 8,092,465 B2 | 1/2012 | Metzger et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,133,234 B2 | 3/2012 | Meridew et al. |
| 8,160,345 B2 | 4/2012 | Pavlovskaia et al. |
| 8,175,683 B2 | 5/2012 | Roose |
| 8,221,430 B2 | 7/2012 | Park et al. |
| 8,234,097 B2 | 7/2012 | Steines et al. |
| 8,241,293 B2 | 8/2012 | Stone et al. |
| 8,282,646 B2 | 10/2012 | Schoenefeld et al. |
| 8,298,237 B2 | 10/2012 | Schoenefeld |
| 8,337,501 B2 | 12/2012 | Fitz et al. |
| 8,337,507 B2 | 12/2012 | Lang et al. |
| 8,343,218 B2 | 1/2013 | Lang et al. |
| 8,366,771 B2 | 2/2013 | Burdulis et al. |
| 8,377,129 B2 | 2/2013 | Fitz et al. |
| 8,439,926 B2 | 5/2013 | Bojarski et al. |
| 8,460,304 B2 | 6/2013 | Fitz et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski |
| 8,585,708 B2 | 9/2013 | Fitz et al. |
| 8,545,569 B2 | 10/2013 | Fitz et al. |
| 8,551,099 B2 | 10/2013 | Lang |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 2003/0055502 A1 | 3/2003 | Lang et al. |
| 2003/0216669 A1 | 11/2003 | Lang et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2005/0234461 A1 | 10/2005 | Burdulis et al. |
| 2005/0267584 A1 | 12/2005 | Burdulis et al. |
| 2006/0111722 A1 | 5/2006 | Bouadi |
| 2007/0083266 A1 | 4/2007 | Lang |
| 2007/0100462 A1 | 5/2007 | Lang et al. |
| 2007/0156171 A1 | 7/2007 | Lang et al. |
| 2007/0157783 A1 | 7/2007 | Chiang |
| 2007/0198022 A1 | 8/2007 | Lang et al. |
| 2007/0226986 A1 | 10/2007 | Park et al. |
| 2007/0233141 A1 | 10/2007 | Park et al. |
| 2007/0233269 A1 | 10/2007 | Steines et al. |
| 2007/0250169 A1 | 10/2007 | Lang |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0195216 A1 | 8/2008 | Philipp |
| 2008/0243127 A1 * | 10/2008 | Lang .................... A61B 5/4528 606/87 |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0024131 A1 | 1/2009 | Metzgu et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0222014 A1 | 9/2009 | Bojarski et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |

(56) References Cited

U.S. PATENT DOCUMENTS

| | | |
|---|---|---|
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0305379 A1 | 12/2011 | Mahfouz |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0179264 A1* | 7/2012 | Todd .................... A61F 2/3877 623/20.2 |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317510 A1 | 11/2013 | Couture et al. |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |

(56) References Cited

U.S. PATENT DOCUMENTS

| | | | |
|---|---|---|---|
| 2014/0039631 A1 | 2/2014 | Bojarski et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0086780 A1 | 3/2014 | Miller et al. | |
| 2014/0277523 A1* | 9/2014 | Masini | A61F 2/3877 623/20.2 |
| 2015/0005772 A1* | 1/2015 | Anglin | A61B 17/158 606/79 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1480111 A | 3/2004 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102365061 A | 2/2012 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 102933163 A | 2/2013 |
| CN | 1729483 B | 10/2013 |
| CN | 103476363 A | 12/2013 |
| CN | 103501731 A | 1/2014 |
| CN | 104379074 A | 2/2015 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1996121 A2 | 12/2008 |
| EP | 2114312 A2 | 11/2009 |
| EP | 2124764 A1 | 12/2009 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |

(56) References Cited

FOREIGN PATENT DOCUMENTS

| | | | |
|---|---|---|---|
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012113030 A1 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Hofmann et al, "Natural-Knee II System", Intermedics Orthopedics, Austin, TX, 1995.
Supplementary European Search Report for EP1928359.

\* cited by examiner

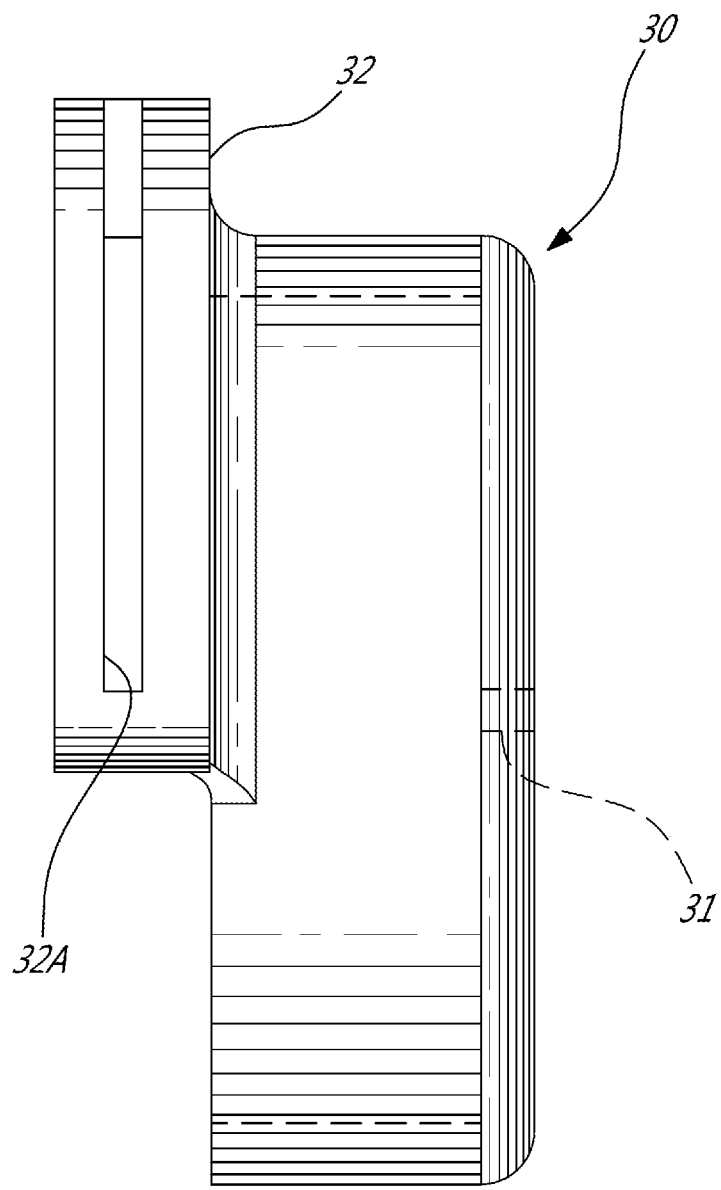

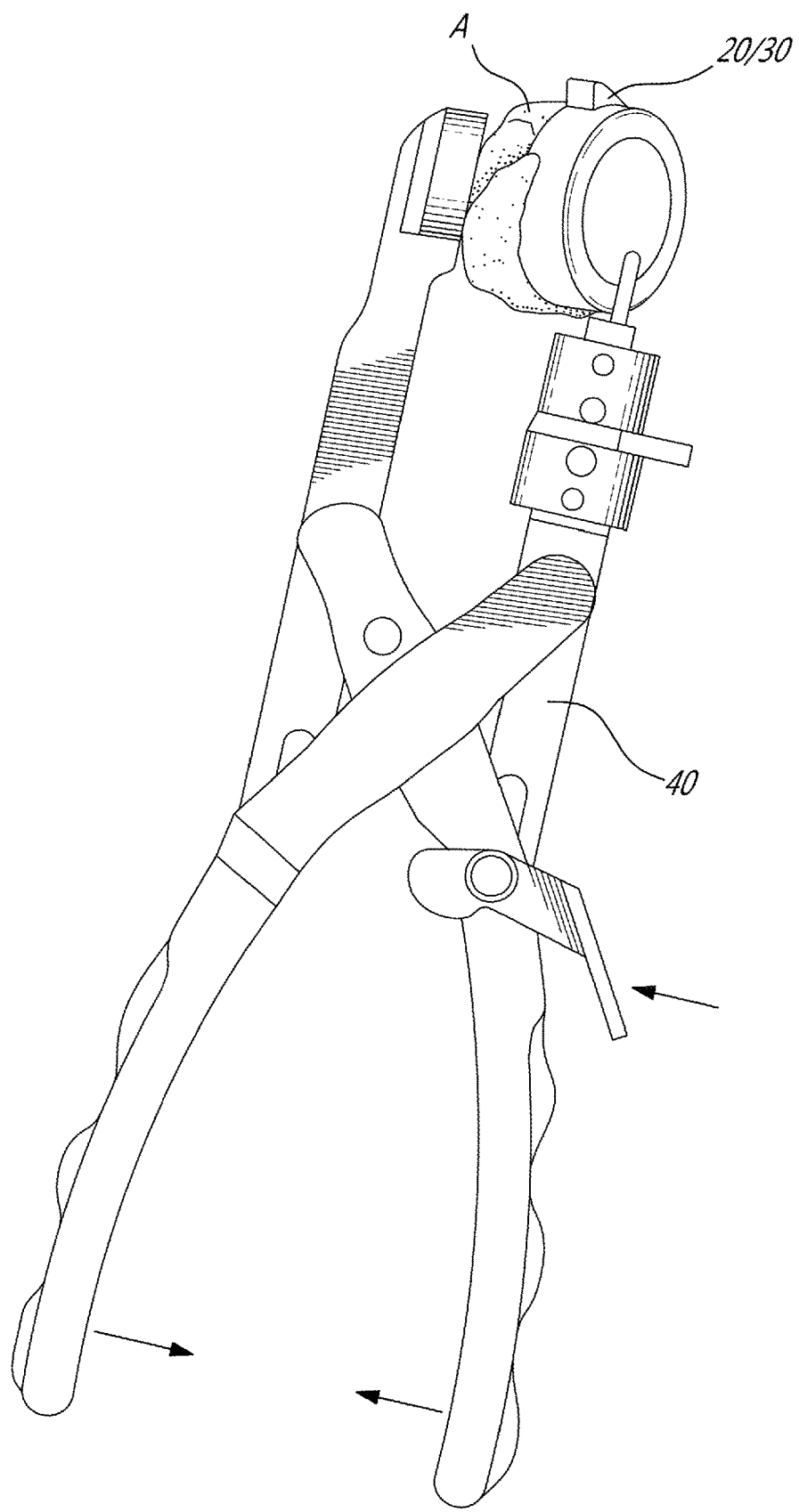

PATIENT-SPECIFIC INSTRUMENTATION FOR PATELLAR RESURFACING SURGERY AND METHOD

CROSS-REFERENCE TO RELATED APPLICATION

The present application claims the priority of U.S. Patent Application Ser. No. 62/235,111, filed on Sep. 30, 2015.

FIELD OF THE INVENTION

The present disclosure pertains to patient specific instrumentation (PSI) used in orthopedic surgery and, more particularly, to PSI used for patellar resurfacing surgery.

BACKGROUND OF THE INVENTION

The patella, also known as a kneecap, is a bone that is positioned anteriorly of the femur at the knee. The patella hence protects the anterior articular surface of the knee joint and plays an active role in knee extension. The patella is connected to the quadriceps by tendon and as such will participate in the leveraging effect produced by the tendon during knee extension.

The patella therefore contacts the femur. In some circumstances, for example knee replacement surgery, the geometric relation between the patella and femur may be altered. This may in turn result in loosening or tensioning in the tendon and ligament connected to the patella and thus cause pain, among other things. Accordingly, patellar implants have been created to act as interfaces between the posterior surface of the patella and the femur (i.e., including any femoral implant), to adjust the spacing between the patella and the femur and balance surrounding soft tissue, such as the quadriceps tendon and the patellar ligament.

SUMMARY OF THE DISCLOSURE

It is an aim of the present disclosure to provide a method for creating a patient-specific jig for patellar resurfacing surgery.

It is a further aim of the present disclosure to provide a method for positioning a patellar implant during surgery.

Therefore, in accordance with a first embodiment of the present disclosure, there is provided a method for creating a patient-specific jig model for patellar resurfacing surgery, the method comprising: obtaining, using one or more processors within a computing system, a patellar model of at least part of a patella, the patellar model being anatomically patient-specific, and an implant model of a patellar implant; obtaining, using the one or more processors within the computing system, a planned position of the patellar implant on the patellar model; calculating, using the one or more processors within the computing system, a position and/or orientation of a resurfacing plane and an attachment bore in the patella as a function of the planned position of the patellar implant; generating, using the one or more processors within the computing system, a virtual jig model corresponding to the resurfacing plane, the attachment bore, and the patellar model, the jig model comprising at least one patient-specific contact surface configured to correspond to a surface of the patella for complementary contact, at least one drill guide positioned relative to the at least one patient-specific contact surface and configured to guide a tool to define the attachment bore in the patella, and at least one cut guide positioned relative to the at least one patient-specific contact surface and configured to guide a tool to resurface the patella to form the resurfacing plane; and outputting, using the one or more processors within the computing system, the jig model.

In accordance with the first embodiment, obtaining the implant model comprises in some instances generating, using the one or more processors within the computing system, a virtual model of the patella using imagery.

Still in accordance with the first embodiment, obtaining the model of the patellar implant comprises in some instances obtaining, using the one or more processors within the computing system, a model of a stock patellar implant.

Still in accordance with the first embodiment, obtaining the planned position of the patellar implant comprises in some instances determining the planned position, using the one or more processors within the computing system, based at least on a native positioning of the patella relative to a femur.

Still in accordance with the first embodiment, determining the planned position comprises in some instances determining the planned position as a function of soft tissue tension.

Still in accordance with the first embodiment, determining the planned position comprises in some instances determining the planned position as a function of planned femoral implant position on the femur.

Still in accordance with the first embodiment, using the one or more processors within the computing system, a position of a pin bore in the patella is calculated in some instances, and wherein generating the virtual jig model comprises in some instances using the pin bore to include another drill guide configured to receive a guide pin to secure the jig during resurfacing.

Still in accordance with the first embodiment, generating the virtual jig model comprises in some instances generating the jig model in a first model portion and a second model portion configured to matingly engage the first model portion, the first model portion having the at least one drill guide, and the second model portion having the at least one cut guide.

Still in accordance with the first embodiment, generating the virtual jig model comprises in some instances generating indicia on the first model portion, the indicia anatomically patient-specific so as to be configured to be aligned with at least one of a proximal-distal axis and a medio-lateral axis.

In accordance with a second embodiment of the present disclosure, there is provided a system for creating a patient-specific jig model for patellar resurfacing surgery, the system comprising: a patellar implant positioning module configured to obtain a planned position of a patellar implant on a patellar model of the patella, the patellar model being anatomically patient-specific; a patella resurfacing calculator module configured to calculate a position and/or orientation of a resurfacing plane and an attachment bore in the patella as a function of the planned position of the patellar implant; and a jig model generator module configured to generate and output a virtual jig model corresponding to the resurfacing plane, the attachment bore, and the patellar model, the jig model comprising at least one patient-specific contact surface configured to correspond to a surface of the patella for complementary contact, at least one drill guide positioned relative to the at least one patient-specific contact surface and configured to guide a tool to define the attachment bore, and at least one cut guide positioned relative to the at least one patient-specific contact surface and configured to guide a tool to resurface the patella to form the resurfacing plane.

In accordance with the second embodiment, a bone model generator module is in some instances provided and configured to generate a virtual model of the patella using imagery.

Still in accordance with the second embodiment, the patellar implant positioning module is in some instances configured to obtain a model of a stock patellar implant.

Still in accordance with the second embodiment, the patellar implant positioning module is in some instances configured to determine the planned position based at least on a native positioning of the patella relative to a femur.

Still in accordance with the second embodiment, the patellar implant positioning module is in some instances configured to determine the planned position as a function of soft tissue tension.

Still in accordance with the second embodiment, the patellar implant positioning module is in some instances configured to determine the planned position as a function of planned femoral implant position on the femur.

Still in accordance with the second embodiment, the patella resurfacing calculator module is in some instances configured to calculate a position of a pin bore in the patella, and wherein the jig model generator module is in some instances configured to generate a second drill guide in the jig model, the second drill guide configured to receive a guide pin to secure the jig during resurfacing.

Still in accordance with the second embodiment, the jig model generator module is in some instances configured to generate the jig model in a first model portion and a second model portion configured to matingly engage the first model portion, the first model portion having the at least one drill guide, and the second model portion having the at least one cut guide.

Still in accordance with the second embodiment, the jig model generator module is in some instances configured to generate the virtual jig model with indicia on the first model portion, the indicia anatomically patient-specific so as to be configured to be aligned with at least one of a proximal-distal axis and a medio-lateral axis.

In accordance with a third embodiment of the present disclosure, there is provided a patient-specific jig for patellar resurfacing surgery, the patient-specific jig comprising: at least one patient-specific contact surface negatively corresponding to a surface of an anatomically patient-specific patella for complementary contact, at least one drill guide positioned relative to the at least one patient-specific contact surface and configured to guide a tool to define an attachment bore in the patella for a patellar implant; and at least one cut guide positioned relative to the at least one patient-specific contact surface and configured to guide a tool to resurface the patella to form a planned resurfacing plane for supporting the patellar implant.

In accordance with the third embodiment, another drill guide is configured in some instances to receive a pin to secure the jig during resurfacing.

Still in accordance with the third embodiment, a first jig portion and a second jig portion are configured in some instances for mating engagement, the first jig portion having the at least one drill guide, the second jig portion having the at least one cut guide.

Still in accordance with the third embodiment, indicia are provided in some instances on the first jig portion, the indicia anatomically patient-specific so as to be configured to be aligned with at least one of a proximal-distal axis and a medio-lateral axis.

In accordance with a fourth embodiment of the present disclosure, there is provided a method for positioning a patellar implant, the method comprising: positioning a jig on a posterior surface of the patella by complementary anatomically patient-specific engagement; machining at least an attachment bore in the posterior surface using the jig; resurfacing the posterior surface of the patella as guided by the jig, such that a portion of the attachment bore remains visible; and anchoring the implant in the attachment bore of the resurfaced patella.

In accordance with the fourth embodiment, the jig is clamped in some instances on the patella prior to machining the attachment bore.

Still in accordance with the first embodiment, a guide pin is inserted in some instances in the jig to secure the jig to the patella.

The feature or features of one embodiment may be applied to other embodiments, even though not described or illustrated, unless expressly prohibited by this disclosure or the nature of the embodiments.

Some details associated with the present embodiments are described above and others are described below.

BRIEF DESCRIPTION OF THE FIGURES

FIG. 5B is a side view of the second portion of the PSI jig on the patella;

FIG. 6 is a perspective view of the PSI jig secured to the patella for resurfacing the patella;

DESCRIPTION OF THE PREFERRED EMBODIMENTS

Figure 1:
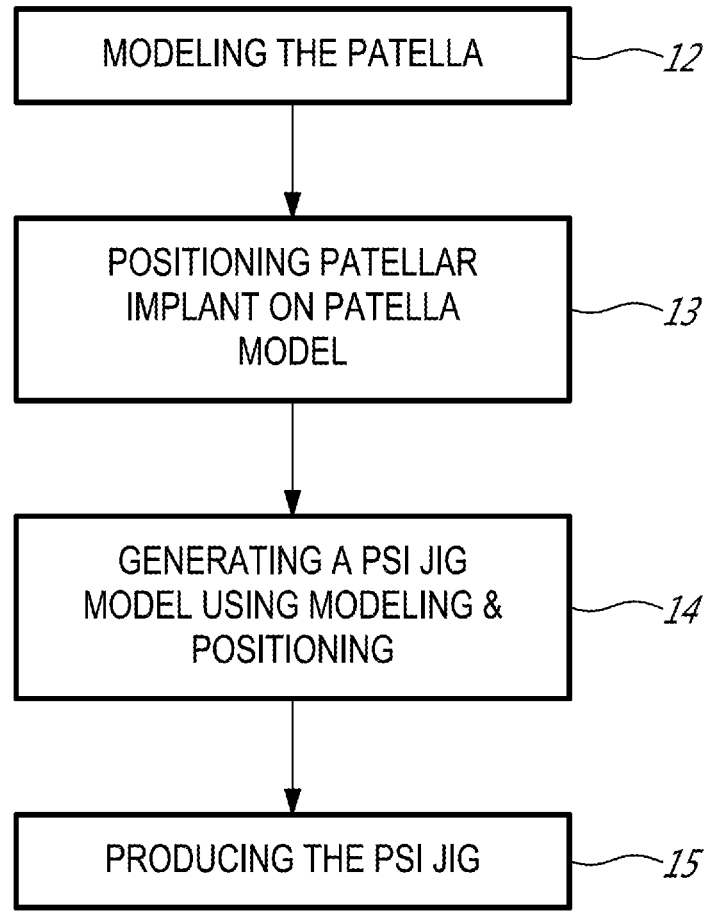
FIG. 1 is a flowchart showing a method for creating a PSI jig for patellar resurfacing surgery in accordance with an embodiment of the present disclosure.

Referring to the drawings, and more particularly to FIG. 1, there is illustrated a method 10 for creating a patient specific instrumentation (hereinafter PSI) jig for patellar resurfacing surgery using one or more processors within a computing system, in which the patella is resurfaced and an implant (prosthesis) is secured to the resurfaced patella. For clarity, reference to patient specific in the present application may pertain to the creation of negative corresponding surfaces, i.e., a surface that is the negative opposite of a patient bone/cartilage surface, such that the patient specific surface conforms to the patient bone/cartilage surface, by complementary confirming contact, enabling a unique positioning of the instrument on the bone. An instrument may also be patient specific in that it is used to plant guide references in a patient's bone, at a specific pre-planned location based on the patient's specific anatomy—the geometry of the instrument is anatomically specific to the patient. The method is particularly suited to be used in conjunction with or subsequent to knee revision in which the femoral knee implant needs to be replaced.

According to 12, the patella is modeled. The model may be obtained and/or generated using imaging, and may be a virtual model, for example in 3D. The imaging may be done by any appropriate technology such as CT scanning (computerized tomography), fluoroscopy, or like radiography methods, providing suitable resolution of images. The model of the patella includes a surface geometry of its posterior surface and other parts of the bone that are exposed. The modeling may include a surface geometry of the adjacent femur with or without implant. In particular, if applicable, a combination of radiography and magnetic resonance imagery (MRI) may provide a suitable resolution between implant, femur and cartilage, useful to recognize the boundaries of the implant relative to the bone. The images of the implant may be confirmed, or the model improved using the manufacturer's model of the existing implant. The bone modeling may comprise generating a 3D surface of the patella if the bone modeling is not directly performed by the imaging equipment, or if not complete. The imaging may also include information relating to surrounding soft tissue. The model of the patella and, if modeled, of the femur with or without implant provides data that may be used by an operator, such as a surgeon, to plan patellar resurfacing surgery.

According to 13, a positioning of the patellar implant model is planned. The patellar implant may be a stock implant, as shown at B on resurfaced patella A in FIG. 9. The planning may also include selecting an implant size from a selection of available patellar implants, the selecting being based on the dimensions of the patella, as obtained from the patellar implant model. The operator may select the position and orientation of a 3D model of a patellar implant (i.e., a new implant) that will be used in surgery, by looking at the model and/or determining locations for cut planes on the patella to support the patellar implant. As the patellar implant may be round as in FIG. 9, the planning may involve determining the location of the center of the patellar implant relative to the patella.

A factor that may come into consideration include native positioning between patella and femur (native meaning the current preoperative state). The positioning of the patellar implant model may include calculating the native positioning between the patella and the femur to assist in reproducing or to provide a corrective value based on the native positioning. Another factor that may affect the positioning of the patellar implant model is the soft tissue tension, such as the tension in the quadriceps tendon and/or in the patellar ligament. The positioning may aim to reduce or increase the tension, during extension and/or flexion. Therefore, an assessment of the soft tissue tension may be done preoperatively, and the information is available in 13 to determine the positioning of the patellar implant model to adjust the soft tissue tension for example by calculating the corrective value to the native positioning. Also, as the patellar resurfacing surgery may occur simultaneously with knee joint replacement, the implant planning for the femur and of the tibia may be taken into consideration in 13. For example, the implanting of a femoral knee implant will cause a change in the contact surface for the patella implant. Therefore, the positioning of the patellar implant model may be based on the planned femoral knee implant position and orientation on the femur, along with the geometry of the femoral knee implant.

As part of the planning of 13, the cut planes of the patella may be determined or selected by the processor, based on a selected patellar implant position and orientation. The cut plane may be based on the thickness of the selected implant, and a desired thickness of the resurfaced patella with implant, for example along the antero-posterior axis.

According to 14, using the patellar model of 12, and the planning of 13, a PSI jig model is generated. The jig model will have a contact surface(s) defined to abut against the posterior surface(s) of the patella obtained in 12, in a predictable and precise manner, although it is considered to position the jig model against other parts of the patella as well, such as the anterior face. Moreover, the PSI reference jig model may have guiding features to guide an operator in positioning landmarks and/or guides in the patella, such that the guiding features are at the planned position and orientation. For example, the PSI jig model may have a cut slot or guide to guide a saw in making a cut plane upon which the patellar implant will be anchored, as well as drill guides for securing the PSI jig to the bone, and/or for positioning an attachment bore in the patella for securing the patellar implant to the resurfaced patella in a planned manner. The drill guide may be used to create an attachment bore for receiving a pin or peg of the patellar implant.

According to 15, once the PSI jig model has been generated, the PSI jig may be output and/or produced, using any appropriate technique, prototyping, 3D printing, casting, etc. The PSI jig model may be a set of executable instructions for 3D printing, machining numerically, etc. The computer system may include an output (screen, monitor, port, transmitter) for the output.

Now that a method for creating a PSI jig for patellar implant surgery has been defined, a method for positioning a patellar implant during surgery is set forth, using the PSI jig as created in the method 10 described above.

Figure 2:
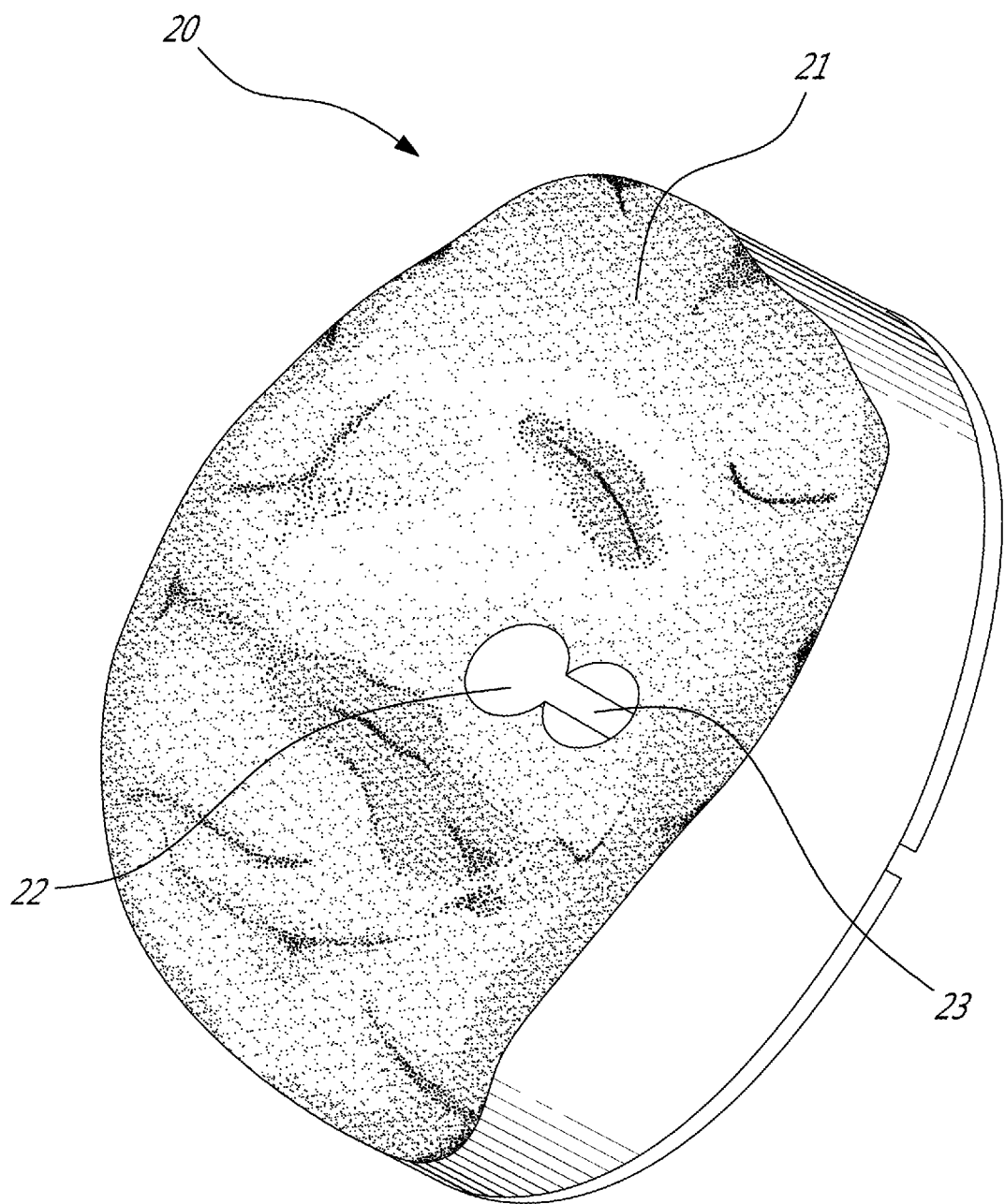
FIG. 2 is a perspective view showing a contour-matching surface of a first portion of the PSI jig.
Figure 3:
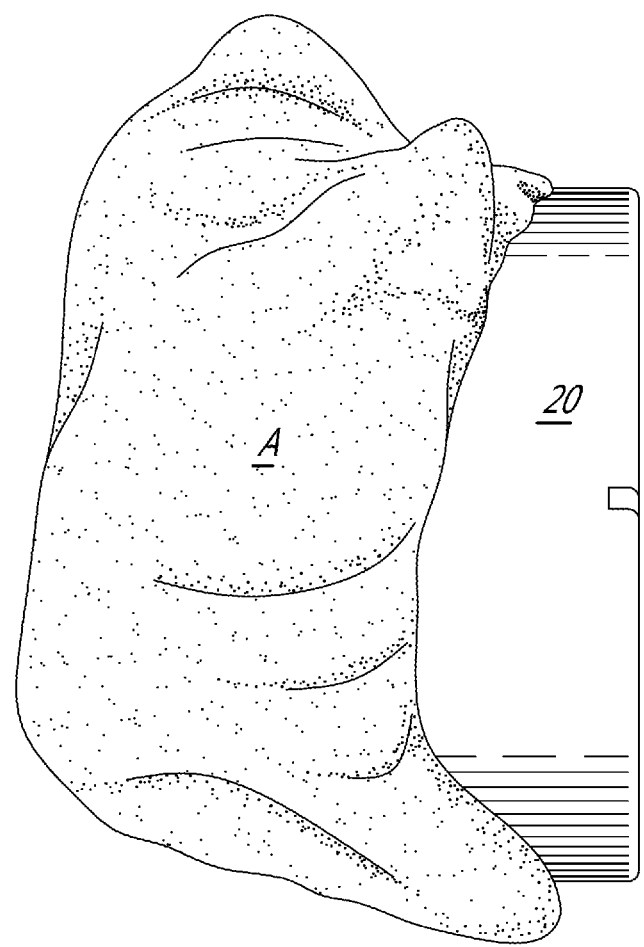
FIG. 3 is a side view showing the first portion of the PSI jig on a patella.
Figure 4:
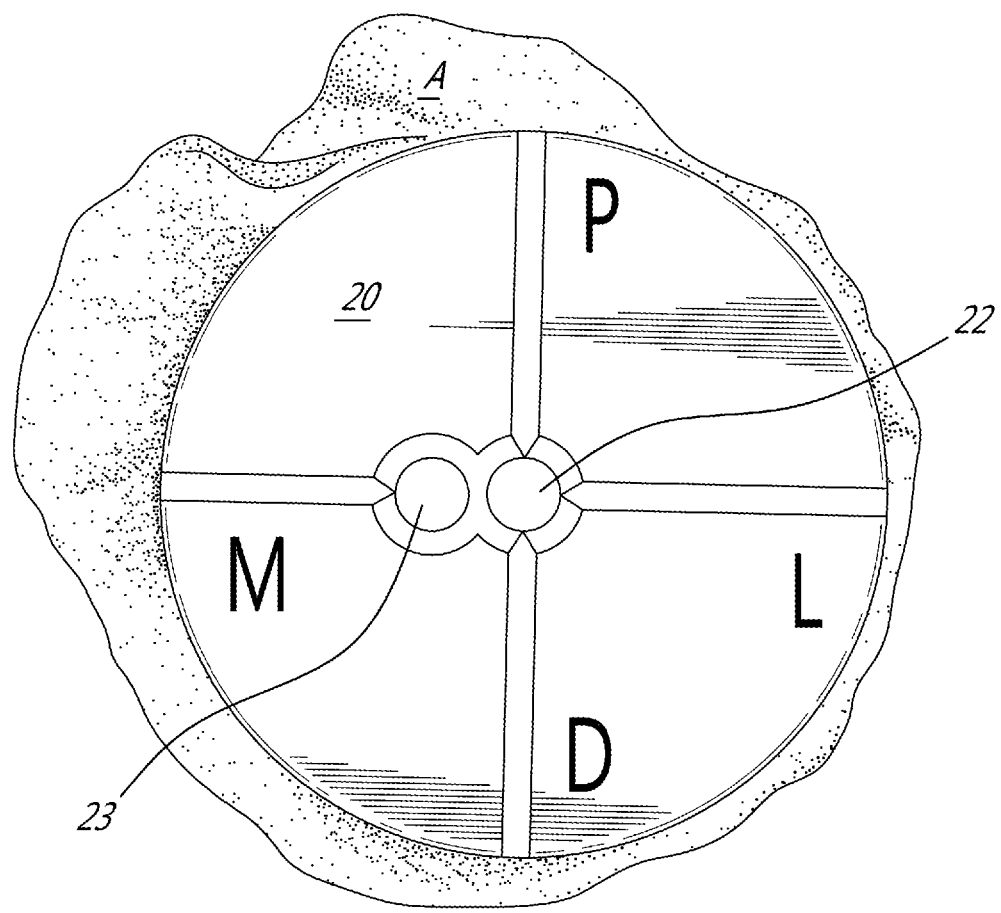
FIG. 4 is a face view of the first portion of the PSI jig on the patella.

Referring to FIGS. 2-4, a first portion of the PSI jig is generally shown as 20. The first portion 20 of the PSI jig has a contour-matching surface 21 (FIG. 2) adapted to contact in complementary engagement the posterior surface of patella A, as in FIGS. 3 and 4, and could also contact other parts of the patella, such as circumferential surfaces and/or the anterior surface of the patella A, in its native state. The first portion 20 may have a pair of drill guides, namely a central drill guide 22 and an offset reference drill guide 23. Moreover, indicia such as ML (medial and lateral) and PD (proximal and distal) axes may be provided on the face of the first portion 20, as guidance or confirmation for the operator. When installing the first portion 20 of the PSI jig on the patella A, the contact surface 21 on the PSI jig is applied against the native posterior surface of the patella A, with a unique complementary match that will ensure that the planned positioning is reached.

Figure 5A:
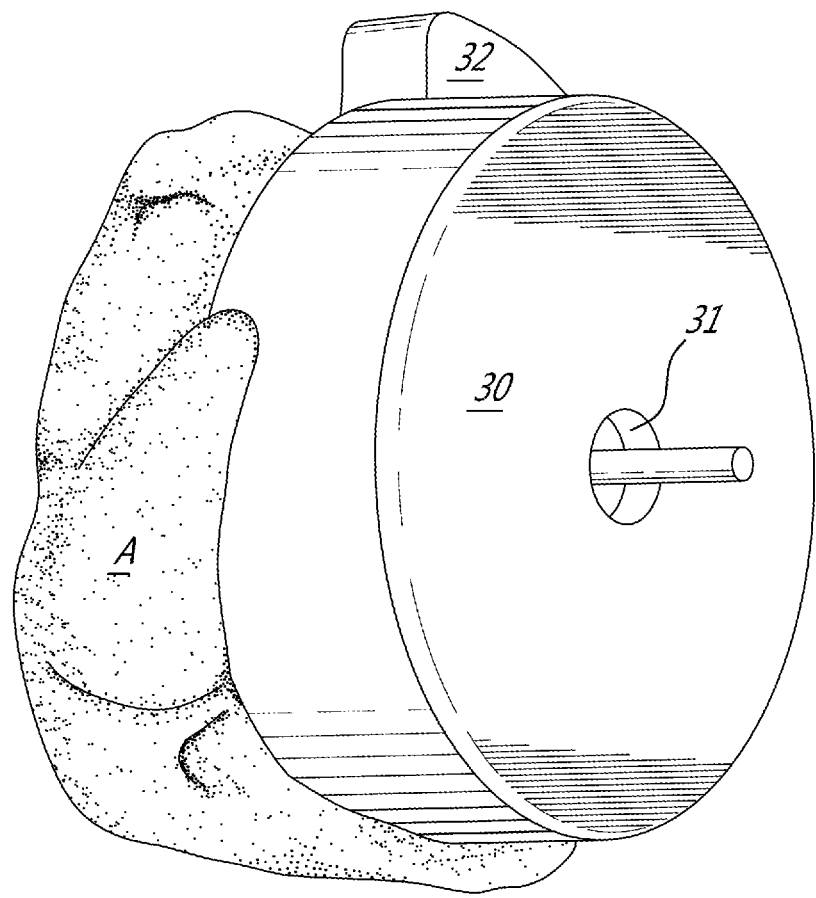
FIG. 5A is a perspective view of a second portion of the PSI jig on the patella.
Figure 7:
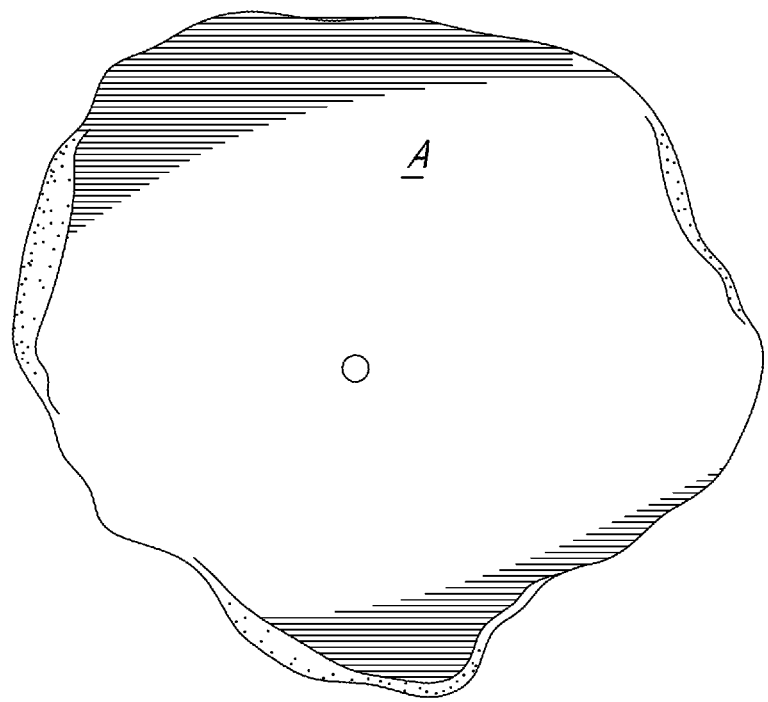
FIG. 7 is a face view of the resurfaced patella.

At that point, the first portion 20 may be anchored to the patella A via the central drill guide 22 and with a pin 24 or like fastener, as in FIG. 5A. Moreover, the attachment bore is drilled using the reference drill guide 23, the attachment bore being deeper than that of the pin 24, as it is intended that the attachment bore resulting from the reference drill guide 23 be present in the resurfaced patella for reception of a peg of the patellar implant, as detailed hereinafter. The attachment bore may indeed serve as reference position for the patellar implant. Alternatively, a single one of the drill guides 22 and 23 may be present. Moreover, due to the PSI nature of the PSI jig, it may not be necessary to use the pin 24. The unique complementary engagement may provide enough stability such that PSI jig may remain in position when manually held. Clamps and other like tools may also be used as alternatives or additionally to the pin 24.

Referring to FIGS. 5A and 5B, once the first portion 20 of the PSI jig is secured to the patella, a second portion 30 of the PSI jig is connected to the first portion 20, by mating engagement. The second portion 30 has a hole 31 to allow passage of the pin 24, for alignment, and a cut guide 32 with a cut slot 32A (FIG. 5B). The cut slot 32A is distanced so as to ensure that the resulting cut plane of the patella is based on the planning (including the thickness of the patellar implant). It is pointed out the first portion 20 and the second portion 30 may be a single PSI jig instead of two interconnected pieces. Moreover, it is contemplated to have integrated metallic components in the cut slot 32A for a body of polymer, etc. According to an embodiment, the second portion 30 is a stock piece while the first portion 20 is a PSI piece. Stated differently, the first portion 20 is manufactured to be anatomically patent specific, in terms of its contact surface 21, of the position of the drill guides 22 and 23 and of its thickness. The second portion 30 may be a stock piece of a more rigid material, such as metal, and hence configured to be reused. The thickness of the first portion 20 is therefore selected as a function of the geometry of the stock second portion 30, to ensure that the cut is located as planned. Therefore, the connection arrangement between the first portion 20 and the second portion 30 may be a male-female tapered engagement with quasi-cylindrical geometries for the first portion 20 and a receiving cavity in the second portion 30.

Referring to FIG. 6, a clamp 40 may then be used to ensure that the PSI jig 20/30 remain anchored in the planned position on the patella A, during the resurfacing of the patella A. The clamp 40 may be any appropriate set of pliers, etc, by which a pressure is applied on the PSI jig 20/30 and on the anterior surface of the patella A. The resecting of the patella may also be done without the clamp 40.

Figure 8:
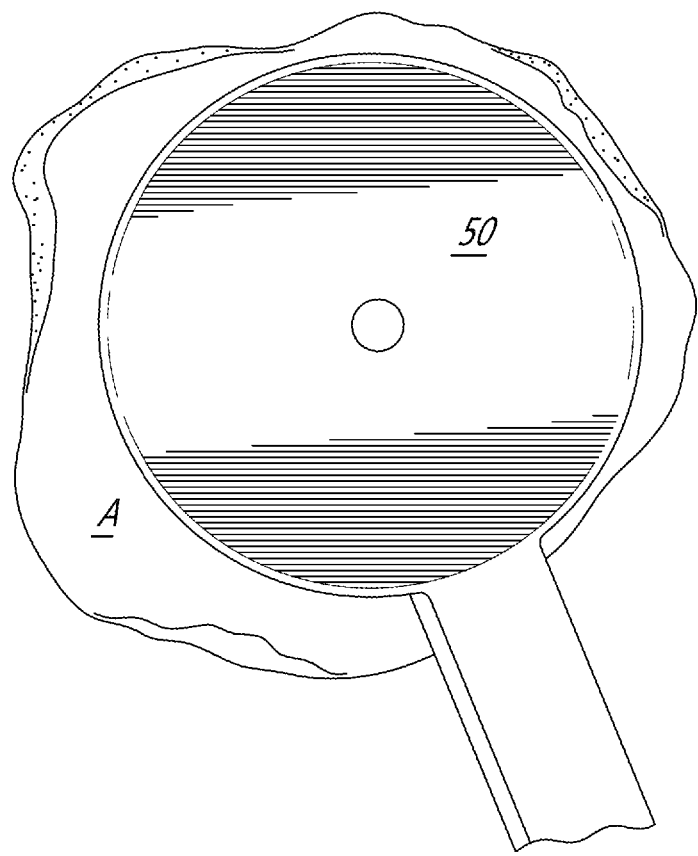
FIG. 8 is a face view of the resurfaced patella of FIG. 7, with a verification jig.
Figure 9:
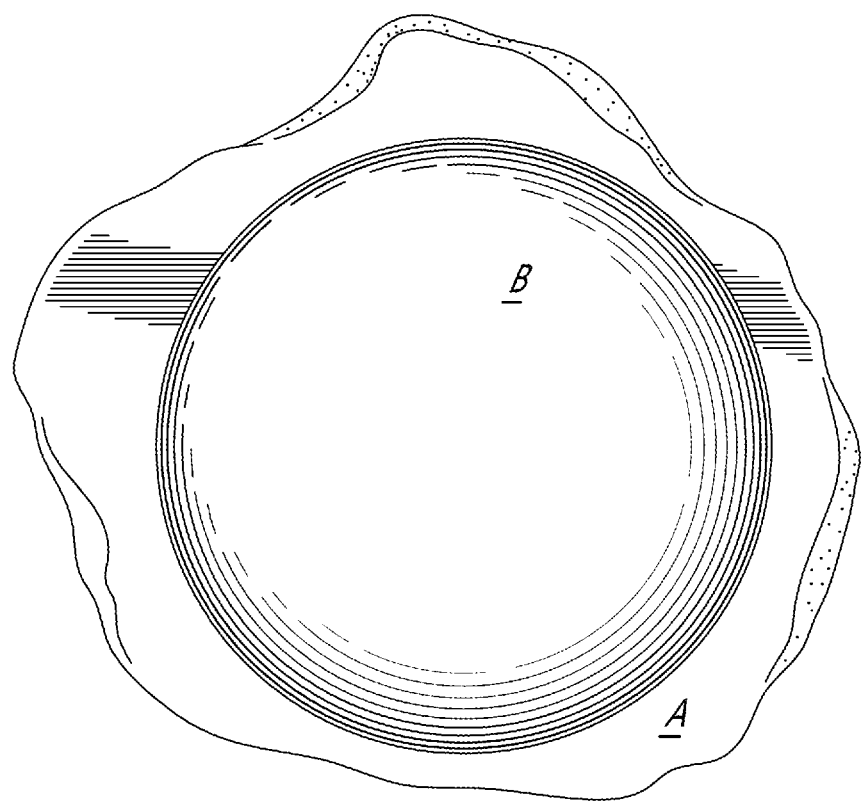
FIG. 9 is a face view of the resurfaced patella with patellar implant.

Once the cut is completed, the patella A is resurfaced, and may have a trace of the bore drilled using the reference drill guide 23. Referring to FIG. 8, a verification jig 50 may be used to ensure that the patellar implant B will not overlap the periphery of the resurfaced patella A, when centered relative to the trace bore. Referring to FIG. 9, the patellar implant B may then be secured to the resurfaced patella A, in the planned position. Although not shown, other machining steps may be performed to anchor the patellar implant B to the resurfaced patella A.

Figure 10:
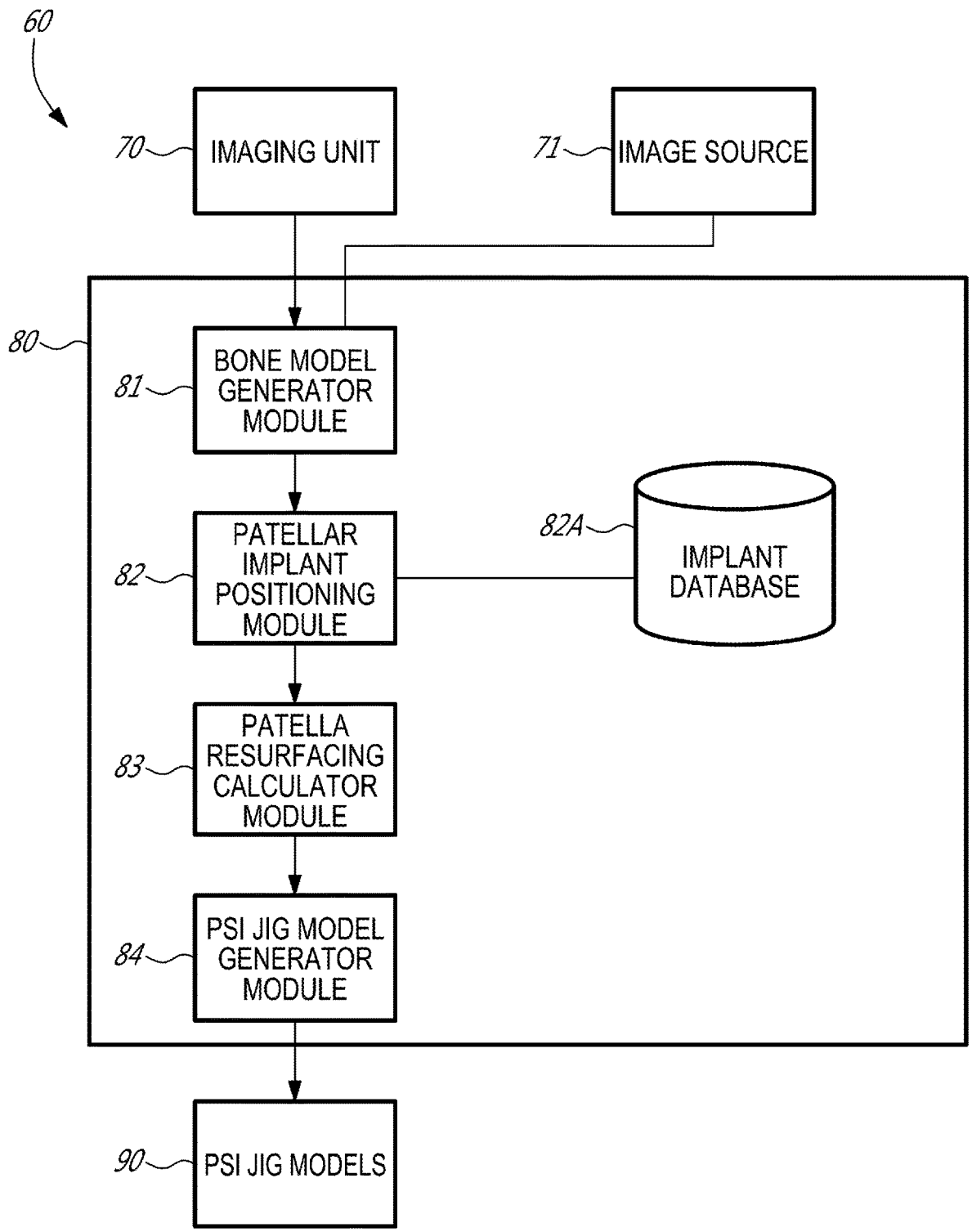
FIG. 10 is a system for creating a PSI jig for patellar resurfacing surgery in accordance with another embodiment of the present disclosure.

Now that the methods for creating a PSI jig for patellar implant surgery and for positioning a patellar implant during surgery have been defined, a system for creating a PSI jig for patellar implant surgery is described and generally shown at 60, in FIG. 10. The system 60 may comprise an imaging unit 70, such as a CT scan or an X-ray machine, so as to obtain images of the patella and surrounding bones and soft tissue. As an alternative, images may be obtained from an image source 71. As an example, a CT scan may be operated remotely from the system 70, whereby the system 70 may simply obtain images and/or processed bone and implant models from the image 71.

The system 70 comprises one or more processors, shown for simplicity as processor 80 (e.g., computer, laptop, etc.) that comprises different modules so as to ultimately produce the jig model(s). The processing unit 80 of the system 60 may therefore comprise a bone model generator module 81 receiving images from sources 70 or 71 to generate a 3D model of the patella. In accordance with the method 10 of FIG. 1, the 3D model of the bone may comprise data pertaining to the surface geometry of a relevant portion of the patella, with or without surrounding bones and soft tissue.

The bone model generator module 81 will create the 3D model of the patella that is then used by a patellar implant positioning module 82 and a patella resurfacing calculator module 83 of the processing unit 80. Alternatively, the modules 82 and 83 may use a 3D model provided by the image source 71, provided the model obtained from the image source 71 comprises sufficient data.

The patellar implant positioning module 82 is used for the virtual planning of the positioning of the patellar implant model. The implant database 82A may provide virtual models of stock patellar implant, as shown at B on resurfaced patella A in FIG. 9. The selection of the implant size may be based on the dimensions of the patella, as obtained from the patellar implant model. The patellar implant positioning module 82 may assist the operator in selecting the position and orientation of the 3D model of the patellar implant that will be used in surgery, by proposing a position and orientation based on the native patella and/or by enabling a relative movement between the models of the patella and of the implant for the operator to virtually select a position and orientation. The patellar implant positioning module 82 may provide data related to the current position to assist the operator, such as the position of the femoral contact surface of the virtual model relative to that of the native patella, for example.

The patellar implant positioning module 82 may factor in soft tissue tension, such as the tension in the quadriceps tendon and/or in the patellar ligament. The positioning of the implant may aim to reduce or increase the tension, during extension and/or flexion. Therefore, the patellar implant positioning module 82 may provide an assessment of the soft tissue tension to allow an adjustment the soft tissue tension for example by calculating the corrective value to the native positioning. Also, as the patellar resurfacing surgery may occur simultaneously with knee joint replacement, the patellar implant positioning module 82 may take into consideration implant planning for the femur and of the tibia. For example, the implanting of a femoral knee implant will cause a change in the contact surface for the patella implant. Therefore, the patellar implant positioning module 82 may base the positioning of the patellar implant model on the planned femoral knee implant position and orientation on the femur, along with the geometry of the femoral knee implant.

The patella resurfacing calculator module 83 of the processing unit 80 calculates the cut planes of the patella based on the selected patellar implant position and orientation output by the patellar implant positioning module 82. The cut plane may be based on the thickness of the selected implant, and a desired thickness of the resurfaced patella with implant, for example along the antero-posterior axis. The patella resurfacing calculator module 83 may factor in the native positioning between patella and femur (native meaning the current preoperative state) in the calculating. The patella resurfacing calculator module 83 of the processing unit 80 may also calculate the location of the center of the patellar implant relative to the patella.

Once the position and orientation of the patellar implant is selected and the cut planes are defined, a PSI jig model generator module 84 may generate a jig model or jig models 90, for instance similar to 20 and 30 shown in FIGS. 2-9. As in 14 of the method 10, the jig model will have a contact surface(s) defined to abut against the patella, in a predictable and precise manner. As the PSI jig will support a tool to perform alterations on the patella, the jig model 90 comprises cutting planes, guides, slots, or any other tooling interface or tool, trackers, oriented and/or positioned to allow bone alterations to be formed in a desired location of the patella, relative to the contact surface(s). Thus, jig model generator module 84 may also take into consideration any planning done by the operator (e.g., surgeon). Accordingly, the system 60 outputs PSI jig model(s) 90 that will be used to create the PSI jig 20/30.

It is considered to use the reference guides as guides for a robotic arm to cut the planes on the bone. In such a case, no jig model would be required. Instead, a navigation file could be provided for a robotic system to perform surgery based on the position and orientation of the patella.

While the methods and systems described above have been described and shown with reference to particular steps performed in a particular order, these steps may be combined, subdivided or reordered to form an equivalent method without departing from the teachings of the present disclosure. Accordingly, the order and grouping of the steps is not a limitation of the present disclosure.

The invention claimed is:

1. A patient-specific jig for patellar resurfacing surgery comprising:
   a first jig portion defining at least one patient-specific contact surface negatively corresponding to a posterior surface of an anatomically patient-specific patella for complementary contact, and at least one drill guide in the first jig portion positioned relative to the at least one patient-specific contact surface to be configured to guide a tool defining an attachment bore in the posterior surface for a single-peg patellar implant, and another drill guide configured to secure a pin for securing the jig during resurfacing, the another drill guide being offset relative to the at least one drill guide and configured for a pin to be offset relative to the attachment bore in the patella; and
   a second jig portion having a part projecting from only a portion of a periphery of the first jig portion, the part defining at least one cut guide positioned relative to the at least one patient-specific contact surface to be configured to guide a tool in resurfacing the patella to form a planned resurfacing plane for supporting the patellar implant.

2. The patient-specific jig according to claim 1, further comprising the first jig portion and the second jig portion concurrently define a male-female mating engagement, the second jig portion having a hole aligned with the another drill guide in the first jig portion for the pin to pass through the hole and the another drill guide.

3. The patient-specific jig according to claim 2, further comprising indicia on the first jig portion, the indicia being anatomically patient-specific so as to be configured to be aligned with at least one of a proximal-distal axis and a medio-lateral axis.

4. The patient-specific jig according to claim 2, wherein the first jig portion and the second jig portion have complementary circular shapes for said mating engagement.

5. The patient-specific jig according to claim 4, wherein the second jig portion has a receiving cavity for said mating engagement of the first jig portion therein.

6. The patient-specific jig according to claim 5, wherein the first jig portion and the second jig portion are substantially cylindrical.

7. The patient-specific jig according to claim 2, wherein the at least one drill guide includes a central drill guide.

8. The patient-specific jig according to claim 7, wherein the hole in the second jig portion is aligned with the central drill guide.

9. The patient-specific jig according to claim 2, further comprising a clamp configured for pressing said mating engagement of the first jig portion and of the second jig portion against the posterior surface of the patella by contacting an anterior surface of the patella.

10. An assembly comprising the patient-specific jig according to claim 1, and a verification jig having a periphery representative of the patellar implant, the verification jig configured to be laid flat against the resurfacing plane of the patella and aligned with the attachment bore.

11. An assembly comprising the patient-specific jig according to claim 1, and the single-peg patellar implant.

12. The assembly according to claim 11, further comprising the pin.

* * * * *